United States Patent [19]
Della Valle et al.

[11] Patent Number: 5,735,863
[45] Date of Patent: Apr. 7, 1998

[54] BIODEGRADABLE AND BIOABSORBABLE GUIDE CHANNELS FOR USE IN NERVE TREATMENT AND REGENERATION

[75] Inventors: Francesco Della Valle, Padua; Aurelio Romeo, Rome; Lanfranco Callegaro, Padua, all of Italy

[73] Assignee: Fidia S.p.A., Abano Terme, Italy

[21] Appl. No.: 104,025

[22] PCT Filed: Feb. 10, 1992

[86] PCT No.: PCT/EP92/00285
§ 371 Date: May 24, 1994
§ 102(e) Date: May 24, 1994

[87] PCT Pub. No.: WO92/13579
PCT Pub. Date: Aug. 20, 1992

[30] Foreign Application Priority Data

Feb. 11, 1991 [IT] Italy ............ PD91A0032

[51] Int. Cl.⁶ .............................................. A61B 17/00
[52] U.S. Cl. .......................... 606/152; 606/154; 623/1; 623/12
[58] Field of Search ............................ 606/152, 151, 606/153–156; 623/11, 12, 1

[56] References Cited

U.S. PATENT DOCUMENTS

| 4,534,349 | 8/1985 | Barrows . | |
|---|---|---|---|
| 4,851,521 | 7/1989 | della Valle . | |
| 5,147,399 | 9/1992 | Dellon et al. | 606/152 |

FOREIGN PATENT DOCUMENTS

| 88/06871 | 9/1988 | WIPO . |
| 89/00431 | 1/1989 | WIPO . |
| 90/05522 | 5/1990 | WIPO . |
| 90/05552 | 5/1990 | WIPO . |

OTHER PUBLICATIONS

Madison et al., Brain Research, 447, 325–334 (1988).
Favaro et al., Trans. Am. Soc. Artif Intern. Organs, 36 M291–M294 (1990).
Williams et al., J. Comparative Neurology, 264, 284–290 (1987).
Politis et al., Brain Research, 253, 1–12 (1982).
Yannas et al., Trans. Soc. Biomat., p. 146 (1985).

Primary Examiner—Jeffrey A. Schmidt
Attorney, Agent, or Firm—Birch, Stewart, Kolasch & Birch, LLP

[57] ABSTRACT

The present invention is drawn to medical devices comprised of biodegradable guide channels for use in repair and regeneration of nerve tissue. The guide channels are comprised of threads embedded in a matrix and coextruded with active factors wherein both the matrix and the threads are comprised of biocompatible and bioabsorbable esters of hyaluronic acid.

19 Claims, 3 Drawing Sheets

BIODEGRADABLE AND BIOABSORBABLE GUIDE CHANNELS FOR USE IN NERVE TREATMENT AND REGENERATION

FIELD OF THE INVENTION

The present invention concerns a medical device comprised of a biodegradable guide channel for use in repair and regeneration of nerve tissue, and for the treatment of trauma to peripheral nerves, as well as methods for the preparation of the guide channels and methods of use.

BACKGROUND OF THE INVENTION

Studies to find alternatives to the surgical techniques commonly used for the treatment of trauma to peripheral nerves have led researchers to experiment with various types of nerve guides as aids in the regeneration of damaged nerves. Most of the research in this field has been focalized on the use of channels or tubular guides which hold the nerve stumps in position while regeneration takes place, biological conditions permitting. These miniature pipelines also avoided or delayed the effects of infiltration involving the connective tissue. Examples of such channels or guides are obtained from various polymers or their derivatives (Ducker et al.: vol. 28, J. Neurosurg. 582–587, 1968; Midgley et al.: vol. 19, Surgical Forum, 519–528, 1968; Lundborg et al.: vol. 41, J. Neuropath. in Exp. Neurol., 412–422, 1982; Molander et al.: vol. 5, Muscle & Nerve, 54–58, 1982; Uzman et al.: vol. 9, J. Neurosci. Res. 325–338, 1983; Nyilas et al.: vol. 29, Transactions Am. Soc. Artif. Internal Organs, 307–313, 1983; U.S. Pat. No. 4,534,349, 1985).

Moreover, to increase functional recovery of the damaged nerve, tubular guides have been prepared with biological polymers (or mixtures of the same) traditionally used in nerve repair (Madison et al.: vol. 44, Brain Res., 325–334., 1985; Yannas et al.: vol. 11, Trans. Soc. Biomat. 146, 1985; Williams et al.: vol. 264, J. Comp. Neurol. 284–290, 1987). There have also been studies to assess the possibility of incorporating various growth factors in the guides (Politis et al.: vol. 253, Brain Res. 1–12, 1982; Aebischer et al.: PCTWO 90/05552).

The problem with using growth factors in guides by the known methods is that the guides are not stable in aqueous solutions, their half-life is measurable in hours rather than weeks, while complete nerve regeneration takes weeks. In these conditions release of the factors cannot be controlled and they are often administered in bolus. Consequently long-term stimulation of the nerve cells involved in regeneration is impossible.

Further progress in the field of nerve guides has been made with the preparation of polymers with which to obtain biocompatible and biodegradable guides which remain in place for varying time periods according to the degree of chemical modification performed on the natural polymer, the type of substitute used (Favero G. et al.: XXXVI Trans. Am. Soc. Artif. Organs, M291–M294, 1990).In this case, too, the nerve stumps are fixed inside the guide by means of a suture, but given the nature of the material used it is possible to obtain selective transport of matter through the channel membrane, thereby creating the ideal environment round the regenerating nerve. These materials combine the advantages of a reabsorbable guide for nervous regeneration with the possibility of creating the best environment for growth. Various methods have been proposed for the construction of guides using biocompatible and bioabsorbable material. The simplest and quickest method is by extruding a biocompatible and bioabsorbable material through a suitable die. The use of guides made with some biocompatible and bioabsorbable materials and produced by extrusion or other manufacturing techniques is limited by their tendency to tear while being surgically stitched to the nerve stump.

There remains, therefore, a need for biocompatible and bioabsorbable guide channels for use in the treatment of damaged nerves, wherein the guide channels are resistant to tearing and provide an enhanced environment for nerve growth in combination with growth factors which stimulate, enhance, or promote nerve regeneration, growth and repair.

SUMMARY OF THE INVENTION

The present invention, therefore, provides improved guide channels comprised of tubular membranes prepared using biocompatible and bioabsorbable polymers, which are rendered tearproof, combined with coextruded, biologically active factors such as growth factors, which are pharmaceutically active on the peripheral nerve system.

The term "active factor" as used herein refers to any substance or compound having bioactivity relative to the nervous system. Such "active factors" preferably have activity to promote, enhance and/or stimulate growth or regeneration of nerve tissue.

DETAILED DESCRIPTION OF THE INVENTION

Figure 1:
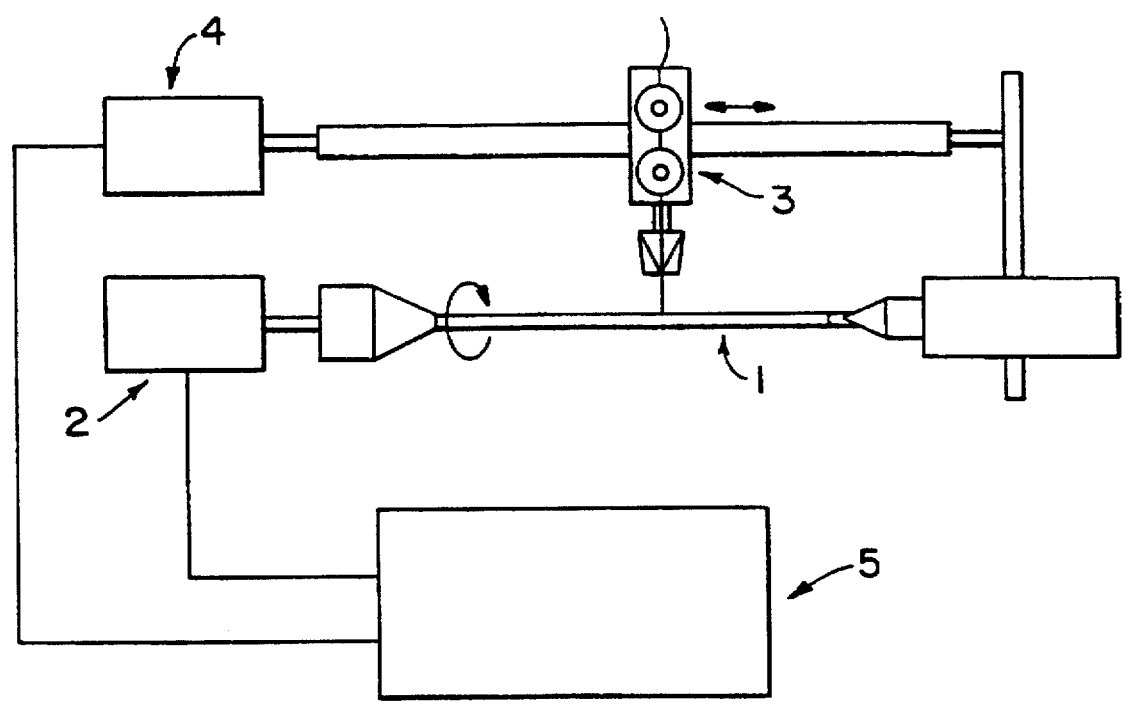
FIG. 1 is a schematic representation of a device useful in the preparation of the nerve guide channels of the present invention.

The guide channels according to the present invention are made of biocompatible and bioabsorbable polymeric materials and are generally between about 5 and 80 mm long, preferably 20 mm, they have an inner diameter of between about 1 and 10 mm, preferably 3 mm, a thickness of between about 80 and 1000 µm, preferably 400 µm and a weight of between 8 and 50 mg (preferably 20 mg) which corresponds to 4–25 mg/cm (preferably 10 mg/cm). Guides made as composite structures are composed of a matrix of biocompatible and bioabsorbable material in which coils of thread of the same material, or of a different but biocompatible and bioabsorbable material, are embedded. The guide channels can also be obtained by embedding a woven tube (smooth weave) in a polymeric matrix. The embedded thread (which can be of a single material or a combination of materials) serves as a reinforcement and as a defense against cracking and tearing of the guide by suture threads or surgical needles. This reinforcement can be comprised of a single strand or of several strands twisted together and can be produced by known extrusion methods, in dry or damp conditions.

The reinforcement threads preferably have a minimum value of 150 denier (UNI 8517/84), a minimum tensile strength at break of 0.4 gr/denier and a minimum elongation of 2% (UNI 1932/86). The minimum number of layers of coiled thread per guide is preferably 2 and preferably 3 per sq cm, in order to obtain a particularly resistent threaded structure. The matrix of biocompatible and bioabsorbable material preferably completely surrounds the threaded reinforcement.

Thus, in the guide channels of the invention the biodegradable threads are embedded in a biodegradable matrix. Embedding the threads in a matrix markedly increases the mechanical characteristics of the product and can preferably be accomplished by a winding manufacturing method, a woven tube manufacturing method or a tubular manufacturing method.

As noted above, both the reinforcement thread and the guide channel matrix are made of a biocompatible and bioabsorbable material. In particular, the guides are made of semisynthetic materials comprised of derivatives of hyaluronic acid, specifically esters of hyaluronic acid. These semisynthetic derivatives of hyaluronic acid are in particular the ester derivatives of hyaluronic acid with pharmacologically inactive alcohols, such as those described in European Patent Publn. No. 0216453 and U.S. Pat. No. 4,851,521. The characteristic which makes these materials particularly suitable for use according to the present invention is that they are not immunogenic and are therefore well tolerated. The guide channels of the invention comprised of esters of hyaluronic acid are, therefore, insoluble in water so as to advantageously form a suitable product, and yet are absorbable by the body (i.e. "bioabsorbable") and are degradable in the body to naturally existing polymers, i.e they are biocompatible.

The Esters of Hyaluronic Acid

Esters of hyaluronic acid useful in the present invention are, therefore, esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters are preferably esters which derive from alcohols which do not themselves possess a notable pharmacological action, such as for example the saturated alcohols of the aliphatic series or simple alcohols of the cycloaliphatic series.

In the above mentioned esters in which some of the carboxylic acid groups remain free (i.e. partial esters), these may be salified with metals or organic bass, such as with alkaline or alkaline earth metals or with ammonia or nitrogenous organic bases.

Most of the esters of hyaluronic acid ("HY"), unlike HY itself, present a certain degree of solubility in organic solvents. This solubility depends on the percentage of esterified carboxylic groups and on the type of alkyl group linked with the carboxyl. Therefore, an HY compound with all its carboxylic groups esterified presents, at room temperature, good solubility for example in dimethylsulfoxide (the benzyl ester of HY dissolves in DMSO in a measure of 200 mg/ml). Most of the total esters of HY present also, unlike HY and especially its salts, poor solubility in water and are essentially insoluble in water. The solubility characteristics, together with particular and notable viscoelastic properties, make the MY esters particularly preferred for use as nerve guide channels.

Alcohols of the aliphatic series to be used as esterifying components of the carboxylic groups of hyaluronic acid for use as guide channels according to the present invention are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or di-hydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably used are those with a maximum of 12, and especially 6 carbon atoms, and in which the hydrocarbyl atoms in the above mentioned amine, ether, ester, thioether, thioester, acetal, ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups may be alkylenamine or alkylencarbamide groups with a maximum of 8 carbon atoms. Of these alcohols, specifically preferred are saturated and non-substituted alcohols, such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols are useful, such as ethyleneglycol, propyleneglycol and butyleneglycol, the trivalent alcohols such as glycerins, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidinylethanol, piperazineylethanol and the corresponding derivatives of normal propyl or normal butyl alcohol, monothioethyleneglycol or its alkyl derivatives, such as the ethyl derivative in the mercaptan function.

Of the higher saturated aliphatic alcohols, preferred are cetyl alcohol and myricyl alcohol, but for the aim of the present invention the higher unsaturated alcohols with one or two double bonds, are especially important, such as especially those contained in many essential oils and with affinity to terpene, such as citronellol, geraniol, nerol, nerolidol, linalool, farnesol, phytol, of the unsaturated lower alcohols it is necessary to consider allyl alcohol and propargyl alcohol. Of the araliphatic alcohols, preferred are those with only one benzene residue and in which the aliphatic chain has a maximum of 4 carbon atoms, which the benzene residue can be substituted by between 1 and 3 methyl or hydroxyl groups or by halogen atoms, especially by chlorine, bromine and iodine, and in which the aliphatic chain may be substituted by one or more functions chosen from the group containing fee amine groups or mono- or dimethylated or by pyrrolidine or piperidine groups. Of these alcohols, most preferred are benzyl alcohol and phenetyl alcohol.

The alcohols of the cycloaliphatic or aliphaticcycloaliphatic series may derive from mono- or polycyclic hydrocarbons, may preferably have a maximum of 34 carbon atoms, may be unsubstituted and may contain one or more substituents, such as those mentioned above for the aliphatic alcohols. Of the alcohols derived from cyclic monoannular hdrocarbons, preferred are those with a maximum of 12 carbon atoms, the rings with preferably between 5 and 7 carbon atoms, which may be substituted for example by between one and three lower alkyl groups, such as methyl, ethyl, propyl or isopropyl groups. As specific alcohols of this group the following are most preferred: cyclohexanol, cyclohexanediol, 1,2,3-cyclohexanetroil and 1,3,5-cyclohexanetriol (phloroglucitol), inositol, and the alcohols which derive from p-methane such as carvomenthol, menthol, and α-γterpineol, 1-terpineol, 4-terpineol and piperitol, or the mixture of these alcohols known as "terpineol", 1,4- and 1,8 terpin. Of the alcohols which derive from hydrocarbons with condensed rings, such as those of the thujane, pinane or comphane, the following are preferred: thujanol, sabinol, pinol hydrate, D and L-borneol and D and L-isoborneol.

Method of Preparing HY Esters of the Invention

Method A

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluenesulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane or aprotic solvents, such as dimethylsulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or according to the other procedure described hereafter, free carboxylic groups of the partial esters may be salified, if desired, in a per se known manner.

Method B

The hyaluronic esters may also be prepared by a method which consists of treating a quaternary ammonium salt of hyaluronic acid with an etherifying agent, preferably in an aprotic organic solvent.

As organic solvents it is preferable to use aprotic solvents, such as dialkylsulphoxides, dialkylcarboxamides, such as in particular lower alkyl dialkylsulphoxides, especially dimethylsulphoxide, and lower alkyl dialkylamides of lower aliphatic acids, such as dimethyl or diethylformamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethylsulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially sodium or potassium salt, in aqueous solution with a salified sulphonic resin with a quaternary ammonium base.

One variation of the previously described procedure consists in reacting a potassium or sodium salt of hyaluronic acid, suspended in a suitable solution such as dimethylsulphoxide, with a suitable alkylating agent in the presence of catalytic quantities of a quaternary ammonium salt, such as iodide of tetrabutylammonium.

For the preparation of the hyaluronic acid esters, it is possible to use hyaluronic acids of any origin, such as for example the acids extracted from the above mentioned natural starting materials, for example from cocks' combs. The preparation of such acids is described in literature: preferably, purified hyaluronic acids are used. Especially used are hyaluronic acids comprising molecular fractions of the integral acids obtained directly by extraction of the organic materials with molecular weights varying within a wide range, for example from about 90%-80% (MW=11.7–10.4 million) to 0.2% (MW=30,000) of the molecular weight of the integral acid having a molecular weight of 13 million, preferably between 5% and 0.2%. Such fractions may be obtained with various procedures described in literature, such as by hydrolyzing, oxydizing, enzymatic or physical procedures, such as mechanical or radiational procedures. Primordial extracts are therefore often formed during these same by publication procedures (for example see the article by Balazs et al. quoted above in "Cosmetics & Toiletries"). The separation and purification of the molecular fractions obtained are brought about by known techniques, for example by molecular filtration.

Additionally useful are purified fractions obtainable from hyaluronic acid, such as for example the ones described in European Patent Publn. No. 0138572.

The salification of HY with the above metals, for the preparation of starting salts for the particular esterification procedure described above, is performed in a per se known manner, for example by reacting HY with the calculated base quantity, for example with alkaline hydrates or with basic salts of such metals, such as carbonates or bicarbonates.

In the partial esters it is possible to salify all the remaining carboxylic groups or only part of them, dosing the base quantities so as to obtain the desired stoichiometric degree of salification. With the correct degree of salification it is possible to obtain esters with a wide range of different dissociation constants and which therefore give the desired pH, in solution or "in situ" at the time of therapeutic application.

PREPARATION EXAMPLES

The following exemplify the preparation of hyaluronic acid esters useful in the guide channels of the invention.

Example 1

Preparation of the (partial) propyl ester of hyaluronic acid (HY)

50% of the esterified carboxylic groups
50% of the salified carboxylic groups (Na)

12.4 g of HY tetrabutylammonium salt with a molecular weight 170,000 corresponding to 20 m.Eq. of a monomeric unit are solubilized in 620 ml of dimethylsulfoxide at 25° C., 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30° C. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

Example 2

Preparation of the (partial) isopropyl ester of hyaluronic acid (HY)—50% of esterified carboxylic groups—50% of salified carboxylic groups (Na)

12.4 g of HY tetrabutylammonium salt with a molecular weight of 160,000 corresponding to 20 m. Eq. of a monomeric unit are solubilized in 620 ml of dimethylsulfoxide at 25° C., 1.8 g (10.6 m.Eq.) of isopropyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial isopropyl ester compound in the title are obtained. Quantitative determination of the ester groups is carried out using the method of R. H. Cundiff and P. C. Markunas [Anal. Chem. 33, 1028–1030 (1961)].

Example 3

Preparation of the (partial) ethyl ester of hyaluronic acid (HY)—75% of esterified carboxylic groups—25% of salified carboxylic groups 12.4 g of HY tetrabutylammonium salt with a molecular weight of 250,000 corresponding to 20 m.Eq. of a monomeric unit are solubilized in 620 ml of dimethylsulfoxide at 25° C., 2.5 g (15.9 m.Eq.) of ethyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.9 g of the partial ethyl ester compound in the title are obtained. Quantitative determination of the ester groups is carried out using the method of R. H. Cundiff and P. C. Markunas [Anal. Chem. 33, 1028–1030, (1961)].

Example 4

Preparation of the (partial) methyl ester of hyaluronic acid (HY)—75% of esterified carboxylic groups—25% of salified carboxylic groups (Na)

12.4 g of HY tetrabutylammonium salt with a molecular weight of 80,000 corresponding to 20 m.Eq. of a monomeric unit are solubilized in 620 ml of dimethylsulfoxide at 25° C., 2.26 g (15.9 m.Eq.) of methyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial methyl ester compound in the title are obtained. Quantitative determination of the ester groups is carried out using the method of R. H. Cundiff and P. C. Markunas [Anal. Chem. 33, 1028–1030 (1961)].

Example 5

Preparation of the methyl ester of hyaluronic acid (HY)

12.4 g of HY tetrabutylammonium salt with a molecular weight of 120,000 corresponding to 20 m.Eq. of a monomeric unit are solubilized in 620 ml of dimethylsulfoxide at 25° C., 3 g (21.2 m.Eq.) of methyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 6

Preparation of the ethyl ester of hyaluronic acid (HY)

12.4 g of HY tetrabutylammonium salt with a molecular weight of 85,000 corresponding to 20 m.Eq. of a monomeric unit are solubilized in 620 ml of dimethylsulfoxide at 25° C., 3.3 g (21.2 m.Eq.) of ethyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 7

Preparation of the propyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 3.6 g (21.2 m.Eq.) of propyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8.3 g of the propyl ester product in the title are obtained. Quantitative determination of the ester groups is carried out using the method of R. H. Cundiff and P. C. Markunas [Anal. Chem. 33, 1028–1030 (1961)].

Example 8

Preparation of the (partial) butyl ester of hyaluronic acid (HY)—50% of esterified carboxylic groups—50% of salified carboxylic groups (Na)

12.4 g of MY tetrabutylammonium salt with a molecular weight of 620,000 corresponding to 20 m.Eq. of a monomeric unit are solubilized in 620 ml of dimethylsulfoxide at 25° C., 1.95 g (10.6 m.Eq.) of n-butyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial butyl ester compound in the title are obtained. Quantitative determination of the ester groups is carried out using the method of R. H. Cundiff and P. C. Markunas [Anal. Chem. 33, 1028–1030 (1961)].

Example 9

Preparation of the (partial) ethoxycarbonylmethyl ester of hyaluronic acid (HY)—75% of esterified carboxylic groups—25% of salified carboxylic groups (Na)

12.4 g of HY tetrabutylammonium salt with a molecular weight of 180,000 corresponding to 20 m.Eq. of a monomeric unit are solubilized in 620 ml of dimethylsulfoxide at 25° C., 2 g of tetrabutylammonium iodide and 1.84 g (15 m.Eq.) of ethyl chloroacetate are added and the resulting solution of kept for 24 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 10 g of the partial ethoxycarbonyl methyl ester compound in the title are obtained.

Quantitative determination of the ethoxylic ester groups is carried out using the method of R. H. Cundiff and P. C. Markunas [Anal. Chem. 33, 1028–1030 (1961)].

Example 10

Preparation of the n-pentyl ester of hyaluronic acid (HY)

12.4 g of HY tetrabutylammonium salt with a molecular weight of 620,000 corresponding to 20 m.Eq. of a monomeric unit are solubilized in 620 ml of dimethylsulfoxide at 25° C., 3.8 g (25 m.Eq.) of n-pentyl bromide and 0.2 g of iodide tetrabutylammonium are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.7 g of the n-pentyl ester product in the title are obtained. Quantitative determination of the ester groups is carried out using the method described on pages 169–172 of Siggia S. and Hann J. G. "Quantitative organic analysis via functional groups" 4th Edition, John Wiley and Sons.

Example 11

Preparation of the isopentyl ester of hyaluronic acid (HY)

12.4 g of HY tetrabutylammonium salt with a molecular weight of 170,000 corresponding to 20 m.Eq. of a monomeric unit are solubilized in 620 ml of dimethysulfoxide at 25° C., 3.8 g (25 m.Eq.) of isopentyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.6 g of the isopentyl ester product featured in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 12

Preparation of the benzylester of hyaluronic acid 12.4 g of HY tetrabutylammonium salt with a molecular weight of 170,000 corresponding to 20 m.Eq. of a monomeric unit are solubilized in 620 ml of dimethylsulfoxide at 25° C., 4.5 g (25 m.Eq.) of benzyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

9 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 13

Preparation of the β-phenylethyl ester of hyaluronic acid (HY)

12.4 g of HY tetrabutylammonium salt with a molecular weight of 125,000 corresponding to 20 m.Eq. of a monomeric unit are solubilized in 620 ml of dimethylsulfoxide at 25° C., 4.6 g (25 m.Eq.) of 2-bromoethylbenzene and 185 mg of tetrabutylammonium iodide are added, and the solution is kept for 12 hours at 30° C.

The resulting mixture is slowly poured into 3,500 ml of ethyl acetate under constant agitation. A precipitate is thus formed which is then filtered and washed four times with 500 ml of ethyl acetate and finally vacuum dried for twenty four hours at 30° C.

9.1 g of the β-phenylethyl ester in the title are obtained. Quantitative determination of the ester groups is carried out according to the method described on page 168–172 of Siggia S. and hanna J. G. "Quantitative organic analysis via functional groups" 4th Edition, John Wiley and Sons.

Example 14

Preparation of the benzyl ester of hyaluronic acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30° C.

3.1 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 15

Preparation of the (partial propyl) ester of hyaluronic acid (HY)—85% of esterified carboxylic groups—15% of salified carboxylic groups (Na)

12.4 g of HY tetrabutylammonium salt with a molecular weight of 165,1000 corresponding to 20 m.Eq. of a monomeric unit are solubilized in 620 ml of dimethysulfoxide at 25° C., 2.9 g (17 m.Eq.) of propyl iodide are added and the resulting solution is kept for 12 hours at 30° C.

A solution is then added containing 62 ml of water and 9 g of sodium chloride and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1.% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial propyl ester compound in the title are obtained. Quantitative determination of the ester groups is carried out using the method of R. H. Cundiff and P. C. Markunas [Anal. Chem. 33, 1028–1030 (1961)].

Example 16

Preparation of the n-octyl ester of hyaluronic acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 4.1 g (21.2 m.Eq.) of 1-bromooctane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the octyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 17

Preparation of the isopropyl ester of hyaluronic acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 2.6 g (21.2 m.Eq.) of isopropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 8.3 g of the isopropyl ester product in the title are obtained. Quantitative determination of the ester groups is carried out using the method of R. H. Cundiff and P. C. Markunas (Anal. Chem. 33, 1028–1030, 1961).

Example 18

Preparation of the 2,6-dichlorobenzyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 5.08 g (21.2 m.Eq.) of 2,6-dichlorobenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.7 g of the 2,6-dichlorobenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 19

Preparation of the 4-terbutylbenzyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.81 g (21.2 m.Eq.) of 4-terbutylbenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.8 g of the 4-terbutylbenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 20

Preparation of the Heptadecyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 6.8 g (21.2 M.Eq.) of Heptadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the Heptadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 21

Preparation of the Octadecyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 7.1 g (21.2 m.Eq.) of octadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the octadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 22

Preparation of the 3-phenylpropyl ester of hyaluronic acid 12.4 g of HY tetrabutylammonium salt with a molecular weight of 170,000 corresponding to 20 m.Eq. of a monomeric unit are solubilized in 620 ml of dimethylsulfoxide at 25° C., 4.22 g (21.2 m.Eq.) of 3-phenylpropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the 3-phenylpropyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 23

Preparation of the 3,4,5-trimethoxybenzvl ester of hyaluronic acid (HY)

12.4 g of HY tetrabutylammonium salt with a molecular weight of 170,000 corresponding to 20 M.Eq. of a monomeric unit are solubilized in 620 ml of dimethylsulfoxide at 25° C., 4.6 g (21.2 m.Eq.) of 3,4,5-trimethoxybenzyl chloride are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 10 g of the 3,4,5-trimethoxybenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 24

Preparation of the Cinnamyl ester of hyaluronic acid (HY)

12.4 g of Hy tetrabutylammonium salt with a molecular weight of 170,000 corresponding to 20 m.Eq. of a monomeric unit are solubilized in 620 ml of dimethylsulfoxide at 25° C., 4.2 9 (21.2 m.Eq.) of Cinnamyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the Cinnamyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 25

Preparation of the Decyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.7 g (21.2 m.Eq.) of 1-bromo decane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.5 g of the Decyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 26

Preparation of the Nonyl ester of hyaluronic acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.4 g (21.2 m.Eq.) of 1-bromo nonane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the Nonyl ester product in the title are obtained. Quantitative determination of the ester groups is carried out using the method described in Siggia S. and Manna J. G. "Quantitative organic analysis via functional groups", 4th Edition, John Wiley and Sons, pages 169–172.

Active Factors

The active factors usable in the guide channels of the invention are particularly those factors which enhance, promote or stimulate regeneration, growth or repair of nerve tissue. There are various factors known to stimulate and enhance nerve regeneration, described for example in Wolicke et al.: vol. 83, Proc. Natl. Acad. Sci., U.S.A. 3012–3016, 1986; Rydel et al.: vol. 1, J. Neurosci. 3639–3653, 1988; Levi Montalcini; vol. 237, Science, 1154–1162, 1987 including the references therein; Brooker et al.: Muscle and Nerve 13, 785–800, 1990. Important growth factors are: Nerve Growth Factor (NGF); Fibroblast Growth Factor (FGF) in its acid (a-FGF) or basic form (b-FGF); Ciliary Neurotrophic Factor (CNTF), Brain Derived Neurotrophic Facor (BDNF), and Neurotropin-3 (NT-3). There are also substances such as gangliosides or their synthetic and semisynthetic derivatives which promote or enhance the biological activity of these growth factors (Vantini et al.: Brain Res. 448, 252–258, 1988). Useful, for example, are naturally existing gangliosides, inner ester ganglioside derivatives such as described in EP Patent No. 0072722 and ester and amide derivatives of gangliosides such as described in EP Patent No. 0167449.

Moreover, the growth factors are preferably human active factors and can be produced by recombinant DNA techniques.

Preparation of the Nerve Guide Channels

Described below are examples of guide channels prepared according to the invention, utilizing the β-form of NGF and CNTF as exemplary active factors. But in general, for the preparation of the guide channels, the active factors are dissolved in suitable quantities in the extrusion bath containing the polymer used to prepare the guides. The nerve guides comprised of wound threads according to the present invention are made with equipment whereby cylindrical steel templates are rotated in synchronisation with the motion of a thread distributor. This equipment can be driven by commercially available motors, while synchronisation can be obtained by mechanical or electronic equipment such that the desired number of coils per sq cm and the desired number of layers is obtained.

The guide channels of the invention are preferably obtained utilizing a "winding method" of production. This system is per se known in industrial manufacturing, but has not previously been applied to the manufacture of nerve guide channels. The present inventors have first succeeded in utilizing a winding method of production to obtain a very high degree of precision and to provide improved nerve guide channels.

According to this procedure, filament winding is usually thought of as a procedure whereby a filament yarn or thread is initially wetted by a resin and then uniformly and regularly wound about a rotating mandrel. The finished pattern is subsequently cured and the mandrel removed.

According to the present invention, a composite structure for use as a nerve guide channel is prepared by utilizing the device schematically shown in FIG. 1. The device set forth in FIG. 1 comprises a cylindrical template 1 in polished AISI 316 steel having an external diameter equal to the internal diameter of the desired nerve guide channel, for example 1.5 mm. The template is mounted so as to revolve on its axis when powered by a suitable motor 2. A thread distributor 3 is mounted so as to move up and down the axis of the steel template 1 and is activated by motor 4. A speed control 5 is provided for independent regulation of the speeds of motors 2 and 4.

A nerve guide channel is produced by distributing a suitable quantity of the hyaluronic acid ester material solution onto the steel template 1, set to rotate at a defined and constant speed. The thread distributor 3 is then set in motion, holding the thread comprised of the hyaluronic acid ester, at a constant speed and at a defined rate of distribution. By running the distributor 3 along the steel template 1 at least twice and removing any excess material with a suitable instrument, a guide channel is obtained with desired characteristics.

As noted above, the wound threads of the hyaluronic acid ester can then also be embedded in a biocompatible, bioabsorbable material, comprised of a hyaluronic acid ester which may be the same or different then the ester utilized to prepare the wound thread.

Therefore, according to the present invention it is possible to produce guides of biocompatible and bioabsorbable material which facilitate nerve reconnection and which are notably resistant to tearing by suture threads or surgical needles and which have, if desired, coextruded growth factors or substances which are biologically or pharmacologically useful for nervous regeneration. The invention also provides a production technique for such guides.

For purely illustrative purposes, the following examples are reported which describe the equipment and processes necessary to obtain guides according to the present invention.

Example 27

A guide made of hyaluronic acid benzyl ester with an esterification percentage of 75% named HYAFF11p75 and composite in structure is obtained using the device shown in FIG. 1.

The guide is made by distributing a suitable quantity of hyaluronic acid benzyl ester solution (between 10 and 50 times the final weight of the guide) onto the steel template set to rotate at a defined and constant speed, for example 115 rpm and then setting in motion the distributor holding hyaluronic acid benzyl ester thread at a constant and defined rate of distribution, for example 14 cm per minute. By running the distributor along the steel template at least twice and removing any excess material with a suitable instrument, a guide channel is obtained which has the following characteristics: length 20 mm, diameter 1.5 mm, thickness 200 µm, 2 layers of coiled thread with a density of 7 coils per square centimeter, total weight 20 mg (which corresponds to 10 mg/cm).

Example 28

A guide made of hyaluronic acid benzyl ester, 75% esterified, named HYAFF11p75 and composite in structure is obtained by coextruding human NGF. The guide is made, as reported in Example 27, by distributing a suitable quantity of hyaluronic acid benzyl ester solution (between 10 and 50 times the final weight of the guide), wherein a suitable quantity, for example 0.5 mg, of the β subunit of human NGF has been dissolved, onto a steel template rotated at a defined and constant speed, for example at 115 rpm and then setting in motion the distributor holding thread made of hyaluronic acid benzyl ester at a defined and constant distribution rate, for example 14 cm per minute. By running the thread distributor along the length of the template at least twice and removing any excess material with a suitable instrument, a guide channel is obtained which has the following characteristics: length 20 mm, diameter 1.5 mm, thickness 200 µm, two layers of coiled thread with a density of seven coils per square centimeter, total weight 20 mg (which corresponds to 10 mg/cm).

Example 29

A guide made of hyaluronic acid benzyl ester, 75% esterified, named HYAFF11p75 and composite in structure is obtained by coextruding human CNTF. The guide is made, as reported in Example 1, by distributing a suitable quantity of a solution of hyaluronic acid benzyl ester (between 10 and 50 times the final weight of the guide) and human CNTF growth factor, onto the steel template set to rotate at a defined and constant speed, for example 115 rpm, and then setting in motion the distributor holding thread made of hyaluronic acid benzyl ester at a constant and defined distribution rate, for example 14 cm per minute. By running the thread distributor at least twice along the length of the steel template and removing any excess material with a suitable instrument, a guide channel is obtained which has the following characteristics: length 20 mm, diameter 1.5 mm, thickness 200 µm, two layers of coiled thread with a density of seven coils per square centimeter, total weight 20 mg (which corresponds to 10 mg/cm).

Example 30

A guide made of hyaluronic acid benzyl ester, 75% esterified, named HYAFF11p75 and composite in structure is obtained by coextruding human BDNF. The guide is made, as reported in Example 27, by distributing a suitable quantity of a solution of hyaluronic acid benzyl ester (between 10 and 50 times the final weight of the guide), and human BDNF growth factor, onto the steel template set to rotate at a defined and constant speed, for example 115 rpm and then setting in motion the distributor holding thread made of hyaluronic acid benzyl ester at a constant and defined distribution rate, for example 14 cm per minute. By running the thread distributor at least twice along the length of the steel template and removing any excess material with a suitable instrument, a guide channel is obtained which has the following characteristics: length 20 mm, diameter 1.5 mm, thickness 200 µm, two layers of coiled thread with a density of seven coils per square centimeter, total weight 20 mg (which corresponds to 10 mg/cm).

Example 31

A guide made of hyaluronic acid benzyl ester, 75% esterified, named HYAFF11p75 and composite in structure is obtained by coextruding a suitable mixture of gangliosides.

The guide is made, as reported in Example 27, by distributing a suitable quantity of a solution of hyaluronic acid benzyl ester (between 10 and 50 times the final weight of the guide) and for example 20 mg of a suitable mixture of gangliosides with the trademark Cronassial, onto the steel template set to rotate at a defined and constant speed, for example 115 rpm and then setting in motion the distributor holding thread made of hyaluronic acid benzyl ester at a constant and defined distribution rate, for example 14 cm per minute. By running the thread distributor at least twice along the length of the steel template and removing any excess material with a suitable instrument, a guide channel is obtained which has the following characteristics: length 20 mm, diameter 1.5 mm, thickness 200 µm, two layers of coiled thread with a density of seven coils per square centimeter, total weight 20 mg (which corresponds to 10 mg/cm).

Example 32

A guide made of hyaluronic acid benzyl ester, 75% esterified, named HYAFF11p75 and composite in structure is obtained by coextruding a suitable mixture of semisynthetic gangliosides.

Coextrusion of the guide is performed as reported in Example 27, by distributing a suitable quantity of a solution of hyaluronic acid benzyl ester (between 10 and 50 times the final weight of the guide), and for example 20 mg of a suitable mixture of semisynthetic gangliosides with the trademark Sinassial® (comprised of the inner esters of $GM_1$, $GD_{1a}$, $GD_{1b}$ and $GT_{1b}$), onto the steel template set to rotate at a defined and constant speed, for example 115 rpm and then setting in motion the distributor holding thread made of hyaluronic acid benzyl ester at a constant and defined distribution rate, for example 14 cm per minute. By running the distributor at least twice along the length of the steel template and removing any excess material with a suitable instrument, a guide channel is obtained which has the following characteristics: length 20 mm, diameter 1.5 mm, thickness 200 μm, two layers of coiled thread with a density of seven coils per square centimeter, total weight 20 mg (which corresponds to 10 mg/cm).

Example 33

A guide channel of total benzyl ester of hyaluronic acid, 100% esterified, named HYAFF11 and with a composite structure of thread/polymeric matrix is thus obtained: A 500 denier thread constituted of HYAFF11 with minimum tensile strength at break 1.3 gr/denier and 23% elongation, was smoothly woven on six needles into a tubular shape with a diameter of 1.5 mm. The tube thus obtained was fitted over a cylindrical template made of AISI 316 polished steel with an external diameter equal to the diameter of the woven tube. The template and tube were then placed on the apparatus described in Example 27. The apparatus was seat in motion and the template thus rotated at a speed of 115 rpm. A suitable quantity of a solution of HYAFF11/dimethylsulfoxide at a concentration of 135 mg/ml was distributed over the rotating template.

The template was then soaked in absolute ethanol to allow coagulation of the HYAFF11/dimethylsulfoxide solution and removal of the tube from the template. The guide channel thus formed is 20 mm long, 350 μm thick, with an internal diameter of 1.5 mm and weight of 25 mg (12.5 mg/cm).

Example 34

A guide channel with a composite structure of thread/polymeric matrix in which the 400 denier thread is constituted of HYAFF11p75 with minimum tensile strength at bread 1.1 gr/denier and 185 elongation, and the polymer matrix is constituted of total HYAFF11, was obtained according to the following procedure.

The thread was smoothly woven on six needles into a tubular shape with a diameter of 1.5 mm. The tube thus obtained was fitted over a cylindrical template made of AISI 316 polished steel with an external diameter equal to the diameter of the woven tube. The template and tube were then placed on the apparatus described in Example 27. The apparatus was set in motion and the template thus rotated at a speed of 115 rpm. A suitable quantity of a solution of HYAFF11/dimethylsulfoxide at a concentration of 135 mg/ml was distributed over the rotating template.

The template was then soaked in absolute ethanol to allow coagulation of the HYAFF11/dimethylsulfoxide solution and removal of the tube from the template. The guide channel thus formed is 20 mm long, 350 μm thick, with an internal diameter of 1.5 mm and weight of 25 mg (12.5 mg/cm).

Example 35

A guide channel with a composite structure of thread/polymeric matrix in which the thread is a mixture of total HYAFF11 (30%) and HYAFF11p75 (70%) and the matrix is composed of total HYAFF11 was obtained according to the following procedure.

A 200 denier total HYAFF11 thread, minimum tensile strength at break 1 gr/denier and 18% elongation, and a 250 denier HYAFF11p75 thread, minimum tensile strength at bread 0.9 gr/denier and 20% elongation are combined by means of a spinning machine to form a single thread composed of the two products.

This thread was smoothly woven on six needles into a tubular shape with a diameter of 1.5 mm. The tube thus obtained was fitted over a cylindrical template made of AISI 316 polished steel with an external diameter equal to the diameter of the woven tube. The template and tube were then placed on the apparatus described in Example 1. The apparatus was set in motion and the template thus rotated at a speed of 115 rpm. A suitable quantity of a solution of HYAFF11/dimethylsulfoxide at a concentration of 135 mg/ml was distributed over the rotating template.

The template was then soaked in absolute ethanol to follow coagulation of the HYAFF11/dimethylsulfoxide solution and removal of the tube from the template. The guide channel thus formed is 20 mm long, 350 μm thick, with an internal diameter of 1.5 mm and weighs 25 mg (12.5 mg/cm).

Pharmacological Tests

The guides obtained according to the present invention can be used as guides for the regeneration of nerves of the peripheral nervous system. For this purpose the guides are fixed to the severed nerve stump by suture, without thereby prejudicing its functional properties and in particular its ability to direct the axonal growth along its interior. The tests described hereafter illustrate the usefulness of the guides, object of the present invention, and demonstrate their functional and bioabsorbable properties.

Test 1

Figure 2:
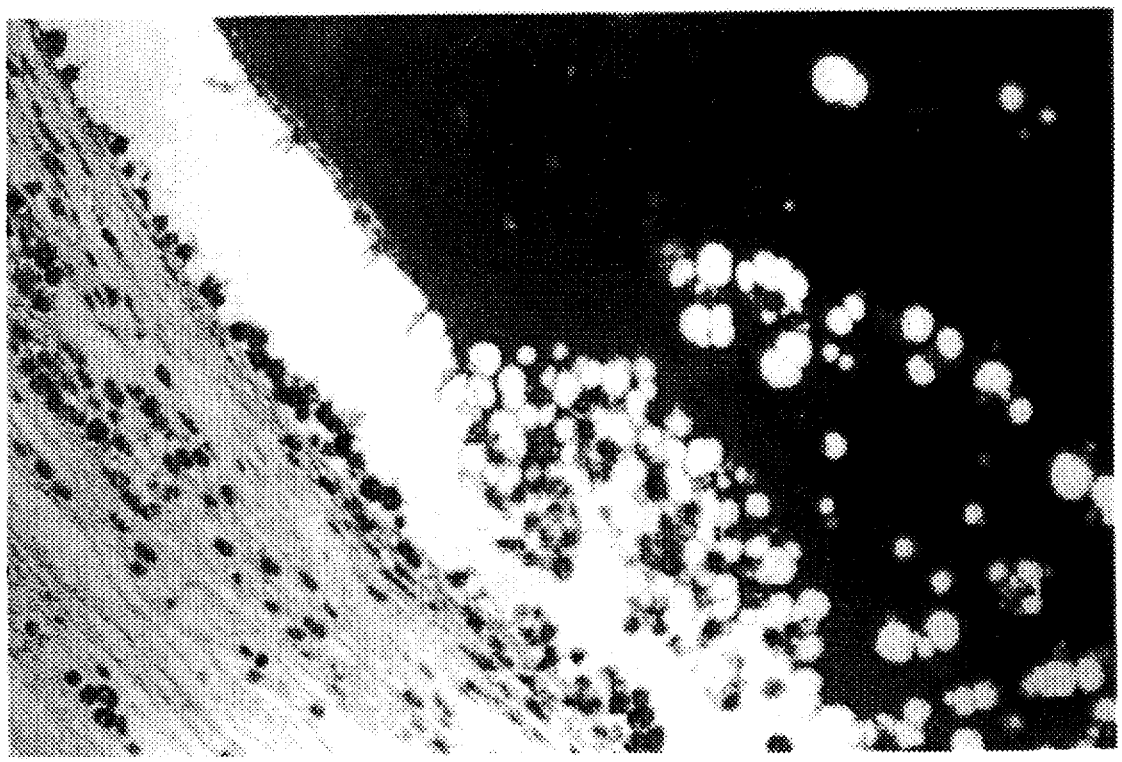
FIG. 2 is an electron micrograph of a nerve guide channel of the invention 10 days post-graft.
Figure 3:
FIG. 3 is an electron micrograph of a nerve guide channel of the invention 4 weeks post-graft.

Rats weighing about 250–300 gr are used for this test. Their sciatic nerves are incised at midpoint. 2 mm of the nerve are removed in order to obtain a gap of 8 mm after spontaneous retraction. The proximal and distal stumps are inserted into a guide as described in one of the previous examples, for instance Example 28 (length 20 mm, diameter 1.5 mm, thickness 200 μm, two layers of coils with a density of 7 coils per square centimeter) previously filled with saline solution and held in place with 9-0 nylon suture. During and after suture the guides remained intact. Ninety days after surgery the regenerated nerves are assessed for function. The results show that the nerve guides, made according to the technique which is object of the present invention, are capable of aiding and directing axonal growth. Further investigation of the regenerated nerves show the bioabsorbability of the guides (FIG. 2), and nerve function recovery (FIG. 3).

The invention being thus described, it is clear that these methods can be modified in various ways. Such modifications are not to be considered as divergences from the spirit and purpose of the invention and any modification which would be apparent to an expert in the field, comes within the scope of the following claims.

We claim:

1. A medical device for use in the treatment of damaged nerve tissue, said device comprising a tubular, biocompatible and bioabsorbable composite of at least two layers of coiled threads which comprises:

a matrix comprised of a biocompatible, bioabsorbable, water-insoluble ester of hyaluronic acid;

a thread embedded in said matrix, said thread being comprised of a biocompatible, bioabsorbable, water-insoluble ester of hyaluronic acid; and an active factor, said factor having activity for treatment of damaged nerve tissue.

2. A medical device according to claim 1, wherein said ester of hyaluronic acid is a total or partial ester of hyaluronic acid with a pharmacologically inactive alcohol.

3. A medical device according to claim 2, wherein said alcohol is an aliphatic, araliphatic, cycloaliphatic or heterocyclic alcohol.

4. A medical device according to claim 3, wherein said aliphatic alcohol is a $C_{1-12}$ aliphatic alcohol.

5. A medical device according to claim 2, wherein said ester is a total ester of hyaluronic acid.

6. A medical device according to claim 2, wherein said ester is a partial ester of hyaluronic acid.

7. A medical device according to claim 2, wherein said aliphatic alcohol is benzyl alcohol.

8. A medical device according to claim 1, wherein said ester of hyaluronic acid is an ester of hyaluronic acid 75% esterified with benzyl alcohol.

9. A medical device according claim 1, wherein said active factor is a member selected from the group consisting of nerve growth factor, ciliary neuronotrophic factor, brain derived neurotrophic factor, neurotropin-3, gangliosides, derivatives of gangliosides, and mixtures thereof.

10. A method of making a medical device according to claim 9, comprising coextruding said active factor and thread in said matrix.

11. A medical device according to claim 1, wherein said device has a minimum value of 150 denier, a minimum tensile strength at break of 0.4 gr/denier and a minimum elongation of 2%.

12. A medical device according to claim 1, wherein said device has a weight of about 4 to 25 mg/cm.

13. A medical device according to claim 1, wherein said device has a thickness of between 80 and 1000 μm.

14. A medical device according to claim 1, wherein the density of the coiled thread is at least 3 coils per $cm^2$.

15. A method of treating a damaged nerve comprising securing said damaged nerve in a medical device of claim 1.

16. The method according to claim 15, wherein said medical device is comprised of a total or partial ester of hyaluronic acid with a pharmacologically inactive alcohol.

17. The method according to claim 16, wherein said alcohol is a $C_{1-12}$ aliphatic alcohol.

18. The method according to claim 16, wherein said alcohol is benzyl alcohol.

19. A process for the preparation of a medical device which comprises winding a thread embedded in a matrix by means of a rotating cylindrical template operatively connected to a thread distributor, wherein said thread and said matrix are comprised of a biocompatible, bioabsorbable, water-insoluble ester of hyaluronic acid.

* * * * *